United States Patent
Stahl et al.

(10) Patent No.: US 7,919,479 B2
(45) Date of Patent: *Apr. 5, 2011

(54) ANTIADHESIVE CARBOHYDRATES

(75) Inventors: Bernd Stahl, Rosbach (DE); Gunther Boehm, Echzell (DE)

(73) Assignee: N. V. Nutricia (NL)

( * ) Notice: Subject to any disclaimer, the term of this patent is extended or adjusted under 35 U.S.C. 154(b) by 743 days.

This patent is subject to a terminal disclaimer.

(21) Appl. No.: 11/511,500

(22) Filed: Aug. 29, 2006

(65) Prior Publication Data

US 2007/0054877 A1 Mar. 8, 2007

Related U.S. Application Data

(63) Continuation of application No. 10/182,739, filed as application No. PCT/EP01/01753 on Feb. 16, 2001, now abandoned.

(30) Foreign Application Priority Data

Feb. 16, 2000 (DE) .................................. 100 06 989

(51) Int. Cl.
*A61K 31/702* (2006.01)
*A61K 31/733* (2006.01)
*A61K 31/732* (2006.01)

(52) U.S. Cl. ................ 514/54; 514/53; 514/61; 424/439

(58) Field of Classification Search .................... None
See application file for complete search history.

(56) References Cited

U.S. PATENT DOCUMENTS

| 4,619,831 A | 10/1986 | Sharma | 426/93 |
| 5,683,991 A | 11/1997 | Guggenbichler et al. | 514/55 |
| 5,952,308 A * | 9/1999 | Nakanishi et al. | 514/25 |

FOREIGN PATENT DOCUMENTS

| DE | 30 46 414 A | 7/1982 |
| DE | 195 03 423 A | 8/1996 |
| JP | 10-226701 | * 8/1998 |
| WO | WO 98 06418 A | 2/1998 |

OTHER PUBLICATIONS

Niness, K. "Inullin and Oligofructose: What are they?" J. Nutr. (1999) vol. 129, pp. 1402S-1406S.*
Caplus abstract of JP 10-226701 (1998).*
Erdman, J. et al "Effects of purified dietary fiber sources . . . " J. Nutr. (1986) vol. 116, pp. 2415-2423.*
Kim, M. et al "Pectin with low molecular weight and high degree of esterification . . . " J. Nutr. (1996) vol. 126, pp. 1883-1890.*
Translation of JP-10226701 (1998).*
Walker, W. et al "Diet and bacterial colonization . . . " J. Nutr. Biochem. (1998) vol. 9, pp. 668-675.*
Akiyama, H. et al "Effect of depolymerized alginates . . . " Biosci. Biotech. Biochem. (1992) vol. 56, No. 2, pp. 355-356.*
Kato et al., (Carbohydrates Research, 227 (1992) 315-329).

* cited by examiner

*Primary Examiner* — Leigh C Maier

(74) *Attorney, Agent, or Firm* — Bacon & Thomas, PLLC

(57) ABSTRACT

Provided is a pharmaceutical or dietetic product, which serves for reducing and/or blocking the adhesion of pathogenic substances and organisms to eucaryontic cells, in particular mammal cells. Said preparation contains at least one carbohydrate having an uronic acid unit on one of the ends thereof. 10 to 100% of the present, terminal uronic acid units pertaining to the carbohydrates are provided with a double bond that is especially situated between the $C_4$ and $C_5$ atom.

9 Claims, No Drawings

ANTIADHESIVE CARBOHYDRATES

This application is a continuation application of pending U.S. application Ser. No. 10/182,739, filed Aug. 14, 2002 (of which the entire disclosure of the pending, prior application is hereby incorporated by reference) which is a 371 of PCT/EP01/01753, filed Feb. 16, 2001.

The invention relates to a pharmaceutical or dietetic preparation for reducing and/or blocking the adhesion of pathogenic substances and organisms to eucaryontic cells, in particular mammal cells, which contains at least one antiadhesive carbohydrate having an uronic acid on one of the ends thereof, and the use of said preparation and the therein contained carbohydrates for the mentioned purposes.

The adhesion of pathogenic organisms, as well as of cell-damaging substances to the surface of mammal cells, is the first step and an indispensable prerequisite for an infection or a damage of the cell. The interaction between the pathogens and the cells is formed by a ligand-receptor relationship, which is thus an important virulence or toxicity factor of the pathogens. As pathogens, at least bacteria, viruses, fungi, monocellular or multicellular parasites, toxins and heavy-metal cations have thereby to be understood. In this ligand-receptor relationship, glycostructures play an important role.

One possibility of at least reducing or completely preventing this ligand-receptor relationship consists in blocking the respective receptors on the cell surface or on the ligand.

Using specific test systems, it could be shown that various carbohydrate mixtures reduce or even completely prevent the adhesion of, for example, micro-organisms to the cell surface, cf.: Kunz, C; Rudloff, S. *Acta Paediatr.* 1993, 82, 903-912. It is thereby assumed that the active carbohydrates have a considerable analogy to the receptor or ligand structures. In the described studies, numerous carbohydrates from animal as well as vegetal origin and also hydrolysis products from vegetal polysaccharides have been used.

The composition and structure of the carbohydrates present in nature and, for example, of the carbohydrates of human milk, are very complex. The same applies, however, for the carbohydrates from vegetal origin and hydrolysis products from vegetal carbohydrates, respectively. Therefrom results that the antiadhesive action of carbohydrates established for pathogens on mammal cells have been effected in the most cases with carbohydrate mixtures and not with purified single structures.

Thus, it is, for example, known that aqueous extracts, as well as juices from various plant products are active against diseases in the intestinal and urogenital tract caused by pathogenic germs. Hence, it is described in the document PCT/EP 94/03006 (WO 95/07084) that by a carrot soup, bladder tea, coconut milk, etc., prepared according to a determined manner, the adherence of pathogenic germs to the epithelial cells of the gastrointestinal and urogenital tract is considerably reduced. It is supposed that the pectins present in the plant products are responsible for this action, which essentially are chains of 1,4-α-glycosidically bound galacturonides. The actually active galacturonides thereby are supposed to comply with various criteria, namely a determined degree of polymerization and methylation.

It is the object of the present invention to show a way how by means of carbohydrates the adhesion of pathogens can efficiently be reduced or prevented by an interaction with ligands and/or superficial structures of eucaryontic cells, and in particular mammal cells.

This task is solved by the teaching of the claims.

The subject matter of the invention therewith is inter alia a pharmaceutical or dietetic preparation containing at least one antiadhesive carbohydrate having an uronic acid unit on one of the ends thereof. As is generally known, carbohydrates have at least two ends, and can even possess three or more ends when they are branched. According to the invention, straight-chain carbohydrates, and also branched-chain carbohydrates may thus be used. On one of these ends, the mentioned uronic acid is present disposing of a terminal COOH group which may be esterified. Preferred uronic acids or uronic acid units thereby are the following free or esterified acids: galacturonic acid, glucuronic acid, guluronic acid, iduronic acid, mannuronic acid, riburonic acid and altruronic acid, the galacturonic acid and glucuronic acid being particularly preferred.

The inventive preparation contains at least one antiadhesive carbohydrate, and hence a determined species having an uronic acid unit on one of the ends thereof. The inventive preparation, however, may also feature several antiadhesive carbohydrates having a terminal uronic acid unit. Appropriately, the inventive preparation contains a mixture of several of such antiadhesive carbohydrates.

As an antiadhesive carbohydrate, such a carbohydrate is understood within the framework of the present documents, which disposes of a terminal uronic acid unit, and namely independent of the fact whether said uronic acid unit has a double bond or not. In other words, the term antiadhesive carbohydrates designates the sum of the carbohydrates having an uronic acid unit featuring a double bond, and those carbohydrates which do dispose of an uronic acid unit, but which have no double bond. An essential idea of the invention consists in that such antiadhesive carbohydrates are used, which feature a minimum content of uronic acid units having a double bond.

The antiadhesive carbohydrates may possess a determined degree of polymerization, which is in general and hence here, as well, abbreviated as DP.

Usually, however, antiadhesive carbohydrates having different DPs are present, with the antiadhesive carbohydrates having a determined degree of polymerization or DP could also be composed in various manners. In other words, the inventive preparation contains at least one determined antiadhesive carbohydrate species having an uronic acid unit on one of the ends thereof. This carbohydrate species, of course, has a determined DP. Moreover, several differently composed antiadhesive carbohydrates may be present having the same DP. In addition, antiadhesive carbohydrates having a different DP may be present, whereby one or several antiadhesive carbohydrate species may be present for each degree of polymerization.

With the definition of the antiadhesive carbohydrates specified above in more detail, which comprise an uronic acid unit on one end, there is not any statement made on the nature of the other saccharide units or monomer units of which these antiadhesive carbohydrates are composed, except that the antiadhesive carbohydrate only consists of one single unit (degree of polymerization=DP 1), namely, one uronic acid unit. Insofar as the antiadhesive carbohydrate has a DP 1, it is exclusively composed of one uronic acid unit of this kind. If the antiadhesive carbohydrate has a DP 2 or higher, then the other saccharide units linked with the uronic acid unit may be of any desired nature.

10 to 100% of the present uronic acid units pertaining to the carbohydrates have to be provided with a double bond. The indication in % thereby indicates the number of the uronic acid units present in toto having a double bond on one of the ends of the carbohydrates with such an uronic acid unit referred to the sum of these uronic acid units having a double bond and the possibly present uronic acid unit having no such double bond on one end of the antiadhesive carbohydrate or antiadhesive carbohydrates.

Incidentally, an uronic acid unit on one end of an antiadhesive carbohydrate here is also referred to as terminal uronic acid unit.

The antiadhesive carbohydrates brought to use according to the invention, which feature such an uronic acid unit on one end, may feature a non-reducing saccharide unit or also a reducing saccharide unit on the other end (in the case of a non-branched chain). Preferably, 10 to 100% of the antiadhesive carbohydrates featuring a terminal uronic acid unit, have such a reducing saccharide unit on the other end (with a straight chain) or on one of the other ends (in the case of a branched chain). In other words, 10 to 100% of the terminal uronic acid units are situated on a non-reducing end. Thus, even all present terminal uronic acid units may be present on the non-reducing end.

Preferably, 50 to 100% of the double bonds are situated between the $C_4$ and $C_5$ atom of the terminal uronic acid units. In this case, too, the indication in % refers to the number of double bonds, independent of the DP of the antiadhesive carbohydrates and the saccharide units forming these antiadhesive carbohydrates. The detection of the double bonds, and hence of the terminal uronic acid units having such a double bond thereby may ensue spectroscopically at 235 nm using the molar extinction coefficient of 5500 l/mol cm, cf. T P Kravtchenko, I. Arnould, A G J Voragen & W. Polnik *Carbohydr. Polymer* 1992, 19, 237-242.

The determination of the carbohydrates having a reducing end ensues by means of the iodometry according to the specifications in: *Analytical Chemistry of Carbohydrates*, H. Scherz, G. Bonn, Editor Thieme Organic Chemistry Monograph Series, Stuttgart, New York, Thieme Publishers 1998, page 32. Carbohydrates having exclusively non-reducing ends may be determined with the usual analytical methods such as osmometry, mass spectrometry (e.g. MALDI-MS, ESI-MS), chromatography (e.g. GPC, HPAEC, HPLC), and capillary electrophoresis, or by a combination of these methods.

The antiadhesive carbohydrates brought to use according to the invention may also feature, apart from the terminal uronic acid units, a non-reducing end, in that, for example, a reducing end is subsequently transformed into a non-reducing end. This may, for example, be achieved by oxidation, reduction or also by linking the reducing end to other molecules. Among these other molecules count, for example, proteins, lipids and technical polymers, whereby (neo)glycoconjugates are obtained. This subsequent modification of the reducing end has no effect on the antiadhesive action of the antiadhesive carbohydrates brought to use according to the invention. These antiadhesive carbohydrates thus may also be immobilized on known carriers via a "formerly" reducing end, for example, on a usual carrier.

When 10 to 100% of the present terminal uronic acid units thus have a double bond, then this, of course, means also that 0 to 90% of the present terminal uronic acid units have no such double bond. Preferably, 10 to 50% of the present terminal uronic acid units of the antiadhesive carbohydrate or of the antiadhesive carbohydrates have such a double bond.

Namely, it has been surprisingly found that in contrast to the teaching of the initially mentioned WO 95/07084, neither the degree of polymerization nor the degree of methylation is responsible for a marked antiadhesive function, even with possibly some of the therein described carbohydrates being allowed to dispose of such a function. Carbohydrates having a terminal uronic acid unit exhibiting a double bond, on the contrary, exercise a marked antiadhesive function. Such antiadhesive carbohydrates and in particular those, the uronic acid unit of which has the double bond situated between the $C_4$ and $C_5$ atom, however, are not obtained according to the teaching of the mentioned WO 95/07084, what will be discussed in more detail hereafter.

When according to the invention, it is the question of an antiadhesive carbohydrate having a given degree of polymerization, then only one single antiadhesive carbohydrate may be concerned. But several differently structured antiadhesive carbohydrates may also be concerned, the common features of which are, for one, the given degree of polymerization and, for another, the terminal uronic acid unit.

Preferably, the inventive preparation exhibits not only one or several antiadhesive carbohydrates having a given DP but several antiadhesive carbohydrates of a different degree of polymerization. The antiadhesive carbohydrates brought to use thereby preferably possess a degree of polymerization of DP 2 up to DP 40, and in particular of DP 2 up to DP 10, and of a maximum of DP 100. Preferably, mixtures of antiadhesive carbohydrates having different chain lengths are therewith used. In this case, too, only one single or several carbohydrate species or any desired plurality of antiadhesive carbohydrate species may be concerned, with an antiadhesive carbohydrate having a determined chain length or a given degree of polymerization.

The antiadhesive carbohydrates having a terminal uronic acid unit situated especially on the non-reducing end and exhibiting a double bond, thus dispose of an increased antiadhesive action. These antiadhesive carbohydrates are also designated as unsaturated carbohydrates within the framework of the present documents.

The inventively used antiadhesive carbohydrates, and hence the unsaturated antiadhesive carbohydrates, as well, may, for example, be obtained in that acidic carbohydrates and preferably uronic acid-containing carbohydrates are cleaved by means of enzymes or chemical cleavage, in such a manner that the indicated contents in uronic acid units having a double bond are obtained. The following may thereby be used as the preferred starter carbohydrates: pectins, pectates, alginates, chondroitins, hyaluronic acids, heparins, heparans, bacterial carbohydrates and other uronic acid-containing carbohydrates. Preferred raw materials in this case are plants and/or parts of plants (such as carrots, citrus fruits, beets and apples, cf. C. Rolin, B U Nielsen & P E Glahn in *Polysaccharides* ed. S. Dimitriu, Marcel Dekker New York 1998. Also algae, animal tissue and bacterial products may be used.

When the unsaturated antiadhesive carbohydrates are prepared by chemical cleavage, then same has to be carried out so that a double bond is introduced via a β-elimination, in that, for example, pectins are split in neutral or weak alkaline conditions, cf. M J H Keijbets & W. Pilnik *Carbohydr. Res.* 1974, 33, 359-362.

The enzymatic cleavage is in particular carried out by means of lyases (such as pectin lyases or pectate lyases) or lyase-containing enzyme preparations.

In the case of the chemical cleavage, one works in neutral to alkaline conditions, so as to thereby obtain the desired content in double bonds. By the appropriate selection of the other parameters such as temperature, pH, and buffer concentration, the degree of esterification of the carboxyl group and/or hydroxyl group may also be influenced. At higher degrees of esterification of the starter compounds used (e.g. pectins), the inventively used antiadhesive carbohydrates and hence the unsaturated antiadhesive carbohydrates, as well, may likewise be obtained with a cleavage carried out in a weak acid range.

The antiadhesive action of the unsaturated antiadhesive carbohydrates is also influenced by the presence of methyl esters of the carboxyl group, as well as of acetyl esters, e.g. on the C-2 and/or C-3 atom of the uronic acids. This applies in particular with the galacturonic acids of the pectins. The degree of methylation or acetylation preferably is 20 to 75%, and in particular 20 to 50%.

As already expounded, the double bond of the uronic acid units situated in particular on the non-reducing end is of special importance in the mixture of antiadhesive carbohydrates preferably brought to use according to the invention. The other saccharide units linked with this uronic acid unit having a double bond or even no such double bond, may be exclusively acidic carbohydrate units, exclusively neutral carbohydrate units, or a mixture of acid and neutral carbohydrate units. Thus namely, the neutral carbohydrate units, as well, influence the antiadhesive action of the unsaturated antiadhesive carbohydrates. Thereby, essentially rhamnose, arabinose, galactose, xylose, glucose, fucose and apiose are concerned, which in turn may be linked with feroyl residues and phenolic substances. This applies in particular to pectins. The portion of neutral carbohydrate units thereby preferably amounts to a maximum of 50%, and in particular to 0 up to 30%.

The antiadhesive action of the antiadhesive carbohydrate brought to use or of the mixture of antiadhesive carbohydrates is not dependent on the concentration in a final product, rather on the supplied amount. Thus, the inventive preparation may exclusively consist of an antiadhesive carbohydrate or of a mixture of antiadhesive carbohydrates. For this purpose, the preparation is, for example, formulated as a tablet or as food supplement. Of course, usual pharmacologically tolerated carriers, diluents and/or adjuvants may be present in the case of a pharmaceutical preparation. These antiadhesive carbohydrates may also be incorporated in any desired food or pharmaceutical preparation containing further ingredients. In the case of food, fats, proteins, minerals, trace elements, vitamins and other materials suited for the production of food may be concerned. In addition, it is possible to use the antiadhesive carbohydrates inventively brought to use in conjunction with other carbohydrates of any desired nature.

According to a preferred embodiment, the other carbohydrates concerned are prebiotic carbohydrate mixtures according to the teaching of WO 00/08948 with the international file number PCT/EP99/05878, and hence a prebiotic carbohydrate mixture of two different, essentially soluble carbohydrate components A and B are concerned, which remain undigested in the gastrointestinal tract and reach the large intestine non-absorbed, with the carbohydrate component A being composed of at least one monosaccharide or of at least one oligosaccharaide (disaccharide up to hexasaccharide) or of a mixture of two or several of these saccharides, with the carbohydrate component B being composed of a polysaccharide (heptasaccharide onwards) or of a mixture of two or several polysaccharides, with the carbohydrate component A=5 up to 95 wt-%, and the carbohydrate component B=5 up to 95 wt-% of the sum of the carbohydrate components A+B (=100 wt-%), and with at least 80 wt-% of the carbohydrates/saccharides of the carbohydrate component A and B being prebiotically active. For the purposes of the present invention, however, only such carbohydrates, which do not represent antiadhesive uronic acid-containing carbohydrates, may form the carbohydrate component A and the carbohydrate component B. Therewith, the components A and B are not ascribed any antiadhesive carbohydrates. These carbohydrates, which form the carbohydrate component A and the carbohydrate component B, are designated as prebiotic carbohydrates in the following for ease of simplification, although only a part of these carbohydrates actually is prebiotically active.

At least 80 wt-% of the carbohydrates called prebiotic or of the saccharides of the sum of the carbohydrate components A and B hence are prebiotically active. Preferably, at least 80 wt-% of the carbohydrates called prebiotic pertaining to the carbohydrate component A, and also at least 80 wt-% of those pertaining to the carbohydrate component B are prebiotically active. In other terms, in each case preferably at least 80 wt-% of the carbohydrates or saccharides called prebiotic of the carbohydrate components A and B have to reach the large intestine undigested (and hence non-absorbable in the small intestine). In other words, the carbohydrates or saccharides of the carbohydrate components A and B are not absorbed and digested in the gastrointestinal tract, neither in the stomach nor in the small intestine, but reach as such the large intestine.

As soluble carbohydrates of the carbohydrate component A and B, those have to be understood, which form in the physical sense a homogenous solution in water in a concentration of at least 1 g/l at room temperature (e.g. according to *Roempps Chemie Lexikon*).

The portion of the non-prebiotically active carbohydrates or saccharides in the carbohydrate components A and B therewith amounts to a maximum of 20 wt-%. With these carbohydrates or saccharides, those are concerned which, it is true, are soluble but can be excreted undigested. These carbohydrates can cause a physical action in that they increase the volume of the faeces or also exercise a water-binding action.

Preferably, the prebiotic carbohydrates/saccharides, which constitute the carbohydrate component A have another structure than the prebiotic carbohydrates/saccharides, which constitute the carbohydrate component B. Further preferred are at least 80 wt-% of the prebiotic carbohydrates/saccharides of the carbohydrate component A and B, namely those which favor lactic acid bacteria and/or are bifidogenous. The weight percentage of the carbohydrate component A is in this case preferably larger than the weight percentage of the carbohydrate component B. The carbohydrate component A preferably constitutes 95 to 60 wt-%, and in particular about 90 wt-%, while the carbohydrate component B constitutes preferably 5 to 40 wt-%, and in particular about 10 wt-%, with A+B=100 wt-%. The prebiotic carbohydrates/saccharides of the carbohydrate components A and B in particular do not exhibit any glucose units in an α1-4 bond and/or an α1-6 bond. The prebiotic carbohydrates/saccharides of the carbohydrate component B are in this case preferably built up by a maximum of up to 100 monosaccharide units.

Further preferred, at least 60 wt-%, and in particular 80 to 100 wt-% of the prebiotic carbohydrates/saccharides of the carbohydrate component A belong to the group of the galactooligosaccharides, and at least 60 wt-%, and in particular 80 to 100 wt-% of the prebiotic carbohydrates/saccharides of the carbohydrate component B belong to the group of the fructopolysaccharides.

If such a prebiotic carbohydrate mixture is present in the inventive preparations, then the weight ratio of the antiadhesive carbohydrate(s) to the prebiotic carbohydrate mixture is preferably 1:99 up to 99:1, and in particular 1:10 up to 10:1, and furthermore in particular about 1:1.

Moreover, apart from the antiadhesive carbohydrates and apart from the possibly present prebiotic carbohydrate mixtures, further usual carbohydrates of any desired kind may also be present in the inventive preparations. Insoluble carbohydrates, soluble as well as digestible carbohydrates, usual carbohydrates primarily serving a nutritive purpose (e.g. starch, maltodextrin, lactose and saccharose) or a mixture of one or several of these carbohydrates may be concerned in this case. The antiadhesive carbohydrates constitute in these cases preferably 0.1 to 30 wt-%, and in particular 1 to 10 wt-%.

It is achieved with the antiadhesive oligosaccharides that pathogenous substances do not bond to mammal cells, or already bonded pathogens are detached. Through the addition of prebiotic oligosaccharides, it is achieved that the dysfunction of the intestinal flora often arising in conjunction with pathogens, is eliminated. Moreover, pathogens in other places outside of the gastrointestinal tract, such as, for example, the urogenital tract, the respiratory tract, the blood system and the skin, are combated by the systemic action of a balanced intestinal flora.

Since the adhesion of pathogens is a prerequisite for their infectivity or toxicity to all cells of the mammal organism, the inventively used antiadhesive carbohydrate may not only be used for preventing or reducing infections or damages in the gastrointestinal tract, rather may be used in all cells.

The subject matter of the invention therefore is also the use of the inventive preparations and the therein contained antiadhesive carbohydrates for preventing or reducing the adhesion of pathogens to eucaryontic cells, and especially mammal cells. Preferably, these carbohydrates are used for the treatment of infections of the gastrointestinal tract, the blood system, the respiratory passages, the urogenital tract, the nasopharyngeal meatus, and for the treatment of damages by toxins or heavy-metal cations of the cells of the gastrointestinal tract, the blood system, the respiratory passages, the urogenital tract, as well as the nasopharyngeal meatus. The subject matter of the invention hence is also the use of the applied antiadhesive carbohydrates for preparing a dietetic or pharmaceutical preparation for the mentioned treatment purposes.

Incidentally, the use is not restricted to enterally administrable food or pharmaceutical preparations. On the contrary, the inventively used antiadhesive carbohydrates may also be used as active agent in non-enterally administrable pharmaceutical preparations. With the inventive preparations, hence, such non-enterally administrable pharmaceutical products may be concerned.

The amount supplied of the inventively used antiadhesive carbohydrates, and therewith the sum of carbohydrates exhibiting a terminal uronic acid unit without a double bond, and of carbohydrates likewise exhibiting a terminal uronic acid unit but having a double bond (unsaturated carbohydrates), with 10 to 100% of the present terminal uronic acid units exhibiting such a double bond, is at least 8 mg/kg per body weight and day, preferably 8 up to 20 mg/kg per body weight and day, and in particular about 10 mg/kg per body weight and day. This indication refers in particular to the preferred unsaturated antiadhesive carbohydrates alone.

When it is the question of ranges within the framework of the present documents, be it, for example, % ranges or mg ranges, then all intermediate values and hence all values lying in between the end values, and all of the narrower ranges covered by these ranges are also disclosed and claimed with these range indications. The indication 8 to 20 mg/kg hence covers all intermediate values, and in particular integer values, e.g. 9, 10, 11, 12, 13, 14, 15, 16, 17, 18, 19 mg/kg. The range indication 10 to 100% hence only constitutes an abbreviated indication for all imaginable intermediate values, and in particular for the integer values 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99%. This applies, for example, for the % indications for the percentage of uronic acid units having a double bond. Also all imaginable narrower ranges are likewise covered and disclosed by this indication. The analog applies to all range indication referring to wt-%, DP or other units.

In the following examples, preferred inventive preparations are described. The examples 1 through 7 concern the preparation of antiadhesive carbohydrates, with at least 10% of the present uronic acid units exhibiting a double bond. The products obtained in this case represent preparations exclusively built up from antiadhesive carbohydrates. The examples 8 and 13 describe mixtures of antiadhesive carbohydrates and a prebiotic carbohydrate mixture in various weight ratios.

EXAMPLE 1

Enzymatic Cleavage 10 g of GENU pectin USP/100 (Hercules Co., Copenhagen, DK) are dissolved in 1 l of 50 mM NaOAc buffer (pH 5.0). 10 ml of pectin-lyase solution (Sigma, Deisenhofen) are added to this solution. The conversion ensues at 40° C. for 24 h. The reaction is stopped by heating to 100° C. for 10 min. The enzyme and non-converted pectin are removed through filtration with a 50 kDa membrane. The filtrate is subsequently freeze-dried.

EXAMPLE 2

Chemical Cleavage 10 g of GENU pectin USP/100 (Hercules Co., Copenhagen, DK) are dissolved in 1 l of 0.2 M of $NH_3$ carbonate buffer (pH 6.8) and heated for 8 h at 80° C. The obtained oligogalacturonides are precipitated as metal salt (e.g. barium salt), filtered, washed, dried, converted into the free acid by means of a DOWEX-50 $H^+$-ion exchanger, and freeze-dried.

EXAMPLE 3

Enzymatic Cleavage 10 g of Laboron pectin X-77 A (C.C.A. Klimmeck, Bad Zwischenahn) are dissolved in 1 l of 50 mM of sodium acetate buffer (pH 4.5). The digestion process is carried out with 1 ml pectin-lyase solution (Gist-Brocades Co., Seclin, France) at 45° C. for 24 h. The reaction is stopped by heating to 95° C. for 5 min. The enzyme and non-converted pectin are removed through gel filtration with BioGel P2 or TosoHaas HW 40 S. The fraction of the oligosaccharides is subsequently freeze-dried.

EXAMPLE 4

Enzymatic Cleavage 10 g of Gruenband pectin (Obipektin, Bischofszell, Switzerland) are dissolved in. 1 l of 50 mM sodium aceate buffer (pH=4.5). 2 ml Pectinex 3 XL (Novo Nordisk Co., Dittingen, Switzerland) are added. The solution is heated to 50° C. for 24 h. The stopping of the reaction ensues by heating to 95° C. for 5 min. The formed oligogalacturonides are precipitated with ethanol, washed and dried.

EXAMPLE 5

Chemical Cleavage 10 g of Gruenband pectin (Obipektin, Bischofszell, Switzerland) are dissolved in 1 l of 0.1 M sodium phosphate buffer (pH 6.8) and heated to 90° C. for 1 h. The released oligogalacturonides are precipitated with ethanol, washed and dried.

EXAMPLE 6

Chemical Cleavage 10 g of GENU pectin USP/100 (Hercules Co., Copenhagen, DK) are dissolved in 1 l of 0.1 M of sodium phosphate buffer (pH 6.8) and heated to 95° C. for 1 h. Long-chain polymers are precipitated with hydrochloric acid at pH 2 and withdrawn by centrifugation. The supernatant including the oligogalacturonides is lyophilized.

EXAMPLE 7

Enzymatic Cleavage 10 g of alginate are dissolved in 1 l of 50 mM NaAc buffer (pH 4.6). 10 ml of alginate-lyase solution are added to this solution. The cleavage ensues at 40° C. for 24 h. The reaction is stopped by heating to 100° C. for 10 min. The enzyme and non-converted alginate are removed through filtration with a 50 kDa membrane. The filtrate subsequently is freeze-dried.

EXAMPLES 8 THROUGH 13

For preparing a preparation that contains, apart from anti-adhesive carbohydrates, also prebiotic carbohydrates, one proceeds as follows.

10 g of oligogalacturonides, which were prepared either by enzymatic cleavage according to any one of the examples 1, 3, 4 and/or 7, or which were prepared by chemical cleavage according to any one of the examples 2, 5 and/or 6, before the drying process, are admixed to and mixed with 10 g of a prebiotic carbohydrate mixture of 9 parts galacto-oligosaccharides (e.g. Elixor, Borculo Co., and Oligomate, Yakult Co.) and 1 part high-molecular inulin (e.g. Raftiline HP, Orafti Co. or Frutafit TEX or EXL., Sensus Co. or Fibruline LC HAT, Cosucra Co.) according to the quantity ratios indicated in the following table.

|  | Example | | | | | |
|---|---|---|---|---|---|---|
| Oligogalacturonides | 8 | 9 | 10 | 11 | 12 | 13 |
| Enzymatic cleavage | 10 g | | 10 g | | 90 g | |
| Chemical cleavage | | 10 g | | 10 g | | 90 g |
| Prebiotic mixture | 10 g | 10 g | 90 g | 90 g | 10 g | 10 g |

Instead of the above-mentioned prebiotic carbohydrate mixture of galacto-oligosaccharides and inulin, carbohydrate mixtures may also be used that are composed of the following components:

α-galacto-oligosaccharides and inulin, β-galacto-oligosaccharides and galactomannans, fructo-oligosaccharides and galactomannans, fructo-oligosaccharides and arabinogalactans, β-galactooligosaccharides and arabinogalactans, as well as xylo-oligosaccharides and glactomannans.

The invention claimed is:

1. A preparation comprising an anti-adhesive carbohydrate or a mixture of antiadhesive carbohydrates having a terminal uronic acid unit on one of the ends thereof, and wherein the antiadhesive carbohydrates have a maximum degree of polymerization of DP 100, 10-50% of the terminal uronic acid units of said antiadhesive carbohydrates have a double bond, and 50 to 100% of the double bonds are situated between the $C_4$ and $C_5$ atom of the terminal uronic acid units, and wherein the degree of esterification of the antiadhesive carbohydrate mixture of antiadhesive carbohydrates with methanol is 20 to 50%; and wherein said preparation contains, apart from the antiadhesive carbohydrate(s), a prebiotic carbohydrate mixture of two different, essentially soluble carbohydrate components A and B, that remain undigested in the gastrointestinal tract and reach the large intestine non-absorbed, that the carbohydrate component A is built up from at least one monosaccharide or from at least one oligosaccharide having from two to six saccharide units or from a mixture of two or several of these saccharides, the carbohydrate component B is built up from a polysaccharide having at least seven saccharide units or from a mixture of two or several polysaccharides, that the carbohydrate component A=5 to 95 wt-%, and the carbohydrate component B=5 to 95 wt-% of the sum of the carbohydrate components A+B and that at least 80 wt-% of the carbohydrates/saccharides of the carbohydrate component A and B are prebiotically active, and that the carbohydrates, which constitute the carbohydrate component A and the carbohydrate component B, do not represent the antiadhesive carbohydrates; and wherein the preparation is a food product.

2. The preparation according to claim 1, further comprising fats, proteins, minerals, trace elements, and vitamins.

3. The preparation according to claim 1, further comprising a component selected from the group consisting of fats, proteins, minerals, trace elements, and vitamins.

4. The preparation of claim 1, characterized in that 10 to 100% of the antiadhesive carbohydrates having a terminal uronic acid unit comprise a reducing end, and comprise the terminal uronic acid unit on another end.

5. The preparation of claim 1, wherein said preparation contains several antiadhesive carbohydrates having a terminal uronic acid unit, which have a different degree of polymerization.

6. The preparation of claim 1, characterized in that the antiadhesive carbohydrates have a maximum degree of polymerization DP 2 up to DP 40.

7. The preparation of claim 1, characterized in that the content of the antiadhesive carbohydrates described in neutral sugar units is a maximum of 50%.

8. A method for treatment of infections of the gastrointestinal tract, the blood system, the respiratory passages, the urogenital tract, and the nasopharyngeal meatus, or damages of the cells of the gastrointestinal tract, the blood system, the respiratory passages, the urogenital tract, and the nasopharyngeal meatus caused by toxins or heavy-metal cations, comprising administering an effective amount of the preparation of claim 1, wherein said antiadhesive carbohydrates of said preparation are administered in a quantity of at least 8 mg/kg per day.

9. The method of claim 8, wherein the antiadhesive carbohydrates of said preparation are administered in a quantity of 8-20 mg/kg per day.

* * * * *